United States Patent
Handique et al.

(10) Patent No.: US 8,216,530 B2
(45) Date of Patent: Jul. 10, 2012

(54) REAGENT TUBE

(75) Inventors: Kalyan Handique, Ypsilanti, MI (US); Theodore Springer, Ann Arbor, MI (US)

(73) Assignee: HandyLab, Inc., Franklin Lakes, NJ (US)

( * ) Notice: Subject to any disclaimer, the term of this patent is extended or adjusted under 35 U.S.C. 154(b) by 0 days.

(21) Appl. No.: 12/904,901

(22) Filed: Oct. 14, 2010

(65) Prior Publication Data

US 2011/0027151 A1    Feb. 3, 2011

Related U.S. Application Data

(63) Continuation of application No. 12/178,557, filed on Jul. 23, 2008, which is a continuation-in-part of application No. 12/218,416, filed on Jul. 14, 2008, and a continuation-in-part of application No. 12/218,498, filed on Jul. 14, 2008, and a continuation-in-part of application No. 12/173,023, filed on Jul. 14, 2008.

(60) Provisional application No. 60/959,437, filed on Jul. 13, 2007.

(51) Int. Cl.
*B01L 3/14* (2006.01)

(52) U.S. Cl. ........ 422/549; 422/913; 422/914; 422/915; 422/916; 422/917; 422/547; 422/550; 422/68.1

(58) Field of Classification Search .................. 422/547, 422/550, 913–918
See application file for complete search history.

(56) References Cited

U.S. PATENT DOCUMENTS

| 1,434,314 | A | 10/1922 | Raich |
| 1,616,419 | A | 2/1927 | Wilson |
| 1,733,401 | A | 8/1930 | Lovekin |
| 3,528,449 | A | 9/1970 | Witte et al. |
| 3,985,649 | A | 10/1976 | Eddelman |
| 4,018,089 | A | 4/1977 | Dzula et al. |
| 4,018,652 | A | 4/1977 | Lanham et al. |
| 4,038,192 | A | 7/1977 | Serur |
| 4,055,395 | A | 10/1977 | Honkawa et al. |
| D249,706 | S | 9/1978 | Adamski |
| 4,139,005 | A | 2/1979 | Dickey |
| D252,157 | S | 6/1979 | Kronish et al. |
| D252,341 | S | 7/1979 | Thomas |
| D254,687 | S | 4/1980 | Fadler et al. |

(Continued)

FOREIGN PATENT DOCUMENTS

CA    2294819    1/1999

(Continued)

OTHER PUBLICATIONS

Brahmasandra et al., On-chip DNA detection in microfabricated separation systems, SPIE Conference on Microfuidic Devices and Systems, 1998, vol. 3515, pp. 242-251, Santa Clara, CA.

(Continued)

*Primary Examiner* — In Suk Bullock
*Assistant Examiner* — Sharon Pregler
(74) *Attorney, Agent, or Firm* — Knobbe Martens Olson & Bear LLP (57) ABSTRACT

A reagent tube configured with a stellated shaped pattern, on its bottom interior surface, configured to facilitate complete or near-complete withdrawal of fluid from the tube, via a pipette tip. The reagent tube may be used for transporting reagents and for carrying out processing operations on biological samples with the reagents, such as preparing polynucleotides extracted from the sample for amplification.

31 Claims, 5 Drawing Sheets

U.S. PATENT DOCUMENTS

| | | | |
|---|---|---|---|
| 4,212,744 A | 7/1980 | Oota | |
| D261,033 S | 9/1981 | Armbruster | |
| D261,173 S | 10/1981 | Armbruster | |
| 4,301,412 A | 11/1981 | Hill et al. | |
| 4,439,526 A | 3/1984 | Columbus | |
| 4,457,329 A | 7/1984 | Werley et al. | |
| 4,466,740 A | 8/1984 | Kano et al. | |
| 4,504,582 A | 3/1985 | Swann | |
| 4,522,786 A | 6/1985 | Ebersole | |
| D279,817 S | 7/1985 | Chen et al. | |
| 4,599,315 A | 7/1986 | Terasaki et al. | |
| 4,612,873 A | 9/1986 | Gunter | |
| 4,612,959 A | 9/1986 | Costello | |
| D288,478 S | 2/1987 | Carlson et al. | |
| 4,654,127 A | 3/1987 | Baker et al. | |
| 4,673,657 A | 6/1987 | Christian | |
| 4,683,195 A | 7/1987 | Mullis et al. | |
| 4,683,202 A | 7/1987 | Mullis | |
| D292,735 S * | 11/1987 | Lovborg | D24/224 |
| 4,720,374 A | 1/1988 | Ramachandran | |
| 4,798,693 A | 1/1989 | Mase et al. | |
| 4,800,022 A | 1/1989 | Leonard | |
| 4,841,786 A | 6/1989 | Schulz | |
| D302,294 S | 7/1989 | Hillman | |
| 4,895,650 A | 1/1990 | Wang | |
| 4,919,829 A | 4/1990 | Gates et al. | |
| 4,921,809 A | 5/1990 | Schiff et al. | |
| 4,935,342 A | 6/1990 | Seligson et al. | |
| 4,946,562 A | 8/1990 | Guruswamy | |
| 4,949,742 A | 8/1990 | Rando et al. | |
| D310,413 S | 9/1990 | Bigler et al. | |
| 4,963,498 A | 10/1990 | Hillman | |
| 4,967,950 A | 11/1990 | Legg et al. | |
| 4,978,502 A | 12/1990 | Dole et al. | |
| 4,978,622 A | 12/1990 | Mishell et al. | |
| 4,989,626 A | 2/1991 | Takagi et al. | |
| 5,001,417 A | 3/1991 | Pumphrey et al. | |
| 5,004,583 A | 4/1991 | Guruswamy et al. | |
| 5,048,554 A | 9/1991 | Kremer | |
| 5,053,199 A | 10/1991 | Keiser et al. | |
| 5,060,823 A | 10/1991 | Perlman | |
| 5,061,336 A | 10/1991 | Soane | |
| 5,064,618 A | 11/1991 | Baker et al. | |
| 5,071,531 A | 12/1991 | Soane | |
| 5,091,328 A | 2/1992 | Miller | |
| D324,426 S | 3/1992 | Fan et al. | |
| 5,096,669 A | 3/1992 | Lauks et al. | |
| 5,126,002 A | 6/1992 | Iwata et al. | |
| 5,126,022 A | 6/1992 | Soane et al. | |
| D328,135 S | 7/1992 | Fan et al. | |
| D328,794 S | 8/1992 | Frenkel et al. | |
| 5,135,627 A | 8/1992 | Soane | |
| 5,135,872 A | 8/1992 | Pouletty et al. | |
| 5,147,606 A | 9/1992 | Charlton et al. | |
| 5,169,512 A | 12/1992 | Wiedenmann et al. | |
| D333,522 S | 2/1993 | Gianino | |
| 5,186,339 A | 2/1993 | Heissler | |
| 5,192,507 A | 3/1993 | Taylor et al. | |
| 5,208,163 A | 5/1993 | Charlton et al. | |
| 5,223,226 A | 6/1993 | Wittmer et al. | |
| D338,275 S | 8/1993 | Fischer et al. | |
| 5,250,263 A | 10/1993 | Manz | |
| 5,252,743 A | 10/1993 | Barrett et al. | |
| 5,256,376 A | 10/1993 | Callan et al. | |
| 5,275,787 A | 1/1994 | Yuguchi et al. | |
| 5,282,950 A | 2/1994 | Dietze et al. | |
| 5,296,375 A | 3/1994 | Kricka et al. | |
| 5,304,477 A | 4/1994 | Nagoh et al. | |
| 5,304,487 A | 4/1994 | Wilding et al. | |
| D347,478 S | 5/1994 | Pinkney | |
| 5,311,896 A | 5/1994 | Kaartinen et al. | |
| 5,311,996 A | 5/1994 | Duffy et al. | |
| 5,316,727 A | 5/1994 | Suzuki et al. | |
| 5,327,038 A | 7/1994 | Culp | |
| 5,339,486 A | 8/1994 | Persic, Jr. | |
| D351,475 S | 10/1994 | Gerber | |
| D351,913 S | 10/1994 | Hieb et al. | |
| 5,364,591 A | 11/1994 | Green et al. | |
| 5,372,946 A | 12/1994 | Cusak et al. | |
| 5,374,395 A | 12/1994 | Robinson | |
| 5,389,339 A | 2/1995 | Petschek et al. | |
| 5,397,709 A | 3/1995 | Berndt | |
| 5,401,465 A | 3/1995 | Smethers et al. | |
| 5,411,708 A | 5/1995 | Moscetta et al. | |
| 5,414,245 A | 5/1995 | Hackleman | |
| 5,416,000 A | 5/1995 | Allen et al. | |
| 5,422,271 A | 6/1995 | Chen et al. | |
| 5,422,284 A | 6/1995 | Lau | |
| 5,427,946 A | 6/1995 | Kricka et al. | |
| 5,474,796 A | 12/1995 | Brennan | |
| D366,116 S | 1/1996 | Biskupski | |
| 5,486,335 A | 1/1996 | Wilding et al. | |
| 5,494,639 A | 2/1996 | Grzegorzewski | |
| 5,498,392 A | 3/1996 | Wilding et al. | |
| 5,503,803 A | 4/1996 | Brown | |
| 5,516,410 A | 5/1996 | Schneider et al. | |
| 5,519,635 A | 5/1996 | Miyake et al. | |
| 5,529,677 A | 6/1996 | Schneider et al. | |
| 5,559,432 A | 9/1996 | Logue | |
| 5,565,171 A | 10/1996 | Dovichi et al. | |
| 5,569,364 A | 10/1996 | Hooper et al. | |
| 5,578,818 A | 11/1996 | Kain et al. | |
| 5,579,928 A * | 12/1996 | Anukwuem | 211/74 |
| 5,580,523 A | 12/1996 | Bard | |
| 5,582,884 A | 12/1996 | Ball et al. | |
| 5,585,069 A | 12/1996 | Zanzucchi et al. | |
| 5,585,089 A | 12/1996 | Queen et al. | |
| 5,585,242 A | 12/1996 | Bouma et al. | |
| 5,587,128 A | 12/1996 | Wilding et al. | |
| 5,589,136 A | 12/1996 | Northrup et al. | |
| 5,593,838 A | 1/1997 | Zanzucchi et al. | |
| 5,595,708 A | 1/1997 | Berndt | |
| 5,599,432 A | 2/1997 | Manz et al. | |
| 5,599,503 A | 2/1997 | Manz et al. | |
| 5,599,667 A | 2/1997 | Arnold, Jr. et al. | |
| 5,601,727 A | 2/1997 | Bormann et al. | |
| 5,603,351 A | 2/1997 | Cherukuri et al. | |
| 5,605,662 A | 2/1997 | Heller et al. | |
| D378,782 S | 4/1997 | LaBarbera et al. | |
| 5,628,890 A | 5/1997 | Carter et al. | |
| 5,630,920 A | 5/1997 | Friese et al. | |
| 5,631,337 A | 5/1997 | Sassi et al. | |
| 5,632,876 A | 5/1997 | Zanzucchi et al. | |
| 5,632,957 A | 5/1997 | Heller et al. | |
| 5,635,358 A | 6/1997 | Wilding et al. | |
| 5,637,469 A | 6/1997 | Wilding et al. | |
| 5,639,423 A | 6/1997 | Northrup et al. | |
| 5,643,738 A | 7/1997 | Zanzucchi et al. | |
| 5,646,039 A | 7/1997 | Northrup et al. | |
| 5,647,994 A | 7/1997 | Tuunanen et al. | |
| 5,651,839 A | 7/1997 | Rauf | |
| 5,652,149 A | 7/1997 | Mileaf et al. | |
| D382,346 S | 8/1997 | Buhler et al. | |
| D382,647 S | 8/1997 | Staples et al. | |
| 5,667,976 A | 9/1997 | Van Ness et al. | |
| 5,671,303 A | 9/1997 | Shieh et al. | |
| 5,674,394 A | 10/1997 | Whitmore | |
| 5,674,742 A | 10/1997 | Northrup et al. | |
| 5,681,484 A | 10/1997 | Zanzucchi et al. | |
| 5,681,529 A | 10/1997 | Taguchi et al. | |
| 5,683,657 A | 11/1997 | Mian | |
| 5,699,157 A | 12/1997 | Parce | |
| 5,700,637 A | 12/1997 | Southern | |
| 5,705,813 A | 1/1998 | Apffel et al. | |
| 5,726,026 A | 3/1998 | Wilding et al. | |
| 5,726,404 A | 3/1998 | Brody | |
| 5,726,944 A | 3/1998 | Taft et al. | |
| 5,731,212 A | 3/1998 | Gavin et al. | |
| 5,744,366 A | 4/1998 | Kricka et al. | |
| 5,747,666 A | 5/1998 | Willis | |
| 5,750,015 A | 5/1998 | Soane et al. | |
| 5,755,942 A | 5/1998 | Zanzucchi et al. | |
| 5,763,262 A | 6/1998 | Wong et al. | |
| 5,770,029 A | 6/1998 | Nelson et al. | |
| 5,770,388 A | 6/1998 | Vorpahl | |
| 5,772,966 A | 6/1998 | Maracas et al. | |
| 5,779,868 A | 7/1998 | Parce et al. | |

| | | | | | |
|---|---|---|---|---|---|
| 5,787,032 A | 7/1998 | Heller et al. | 6,010,607 A | 1/2000 | Ramsey |
| 5,788,814 A | 8/1998 | Sun et al. | 6,010,608 A | 1/2000 | Ramsey |
| 5,800,690 A | 9/1998 | Chow et al. | 6,010,627 A | 1/2000 | Hood, III |
| 5,804,436 A | 9/1998 | Okun et al. | 6,012,902 A | 1/2000 | Parce |
| D399,959 S | 10/1998 | Prokop et al. | D420,747 S | 2/2000 | Dumitrescu et al. |
| 5,827,481 A | 10/1998 | Bente et al. | D421,130 S | 2/2000 | Cohen et al. |
| 5,842,106 A | 11/1998 | Thaler et al. | 6,024,920 A | 2/2000 | Cunanan |
| 5,842,787 A | 12/1998 | Kopf-Sill et al. | D421,653 S | 3/2000 | Purcell |
| 5,846,396 A | 12/1998 | Zanzucchi et al. | 6,033,546 A | 3/2000 | Ramsey |
| 5,849,208 A | 12/1998 | Hayes et al. | 6,043,080 A | 3/2000 | Lipshutz et al. |
| 5,849,486 A | 12/1998 | Heller et al. | 6,046,056 A | 4/2000 | Parce et al. |
| 5,849,489 A | 12/1998 | Heller | 6,048,734 A | 4/2000 | Burns et al. |
| 5,849,598 A | 12/1998 | Wilson et al. | 6,054,034 A | 4/2000 | Soane et al. |
| 5,852,495 A | 12/1998 | Parce | 6,054,277 A | 4/2000 | Furcht et al. |
| 5,856,174 A | 1/1999 | Lipshutz et al. | 6,056,860 A | 5/2000 | Amigo et al. |
| 5,858,187 A | 1/1999 | Ramsey et al. | 6,057,149 A | 5/2000 | Burns et al. |
| 5,858,188 A | 1/1999 | Soane et al. | 6,062,261 A | 5/2000 | Jacobson et al. |
| 5,863,502 A | 1/1999 | Southgate et al. | 6,063,341 A | 5/2000 | Fassbind et al. |
| 5,863,708 A | 1/1999 | Zanzucchi et al. | 6,063,589 A | 5/2000 | Kellogg et al. |
| 5,863,801 A | 1/1999 | Southgate et al. | 6,071,478 A | 6/2000 | Chow |
| 5,866,345 A | 2/1999 | Wilding et al. | 6,074,725 A | 6/2000 | Kennedy |
| 5,869,004 A | 2/1999 | Parce et al. | 6,074,827 A | 6/2000 | Nelson et al. |
| 5,872,010 A | 2/1999 | Karger et al. | D428,497 S | 7/2000 | Lapeus et al. |
| 5,872,623 A | 2/1999 | Stabile et al. | 6,086,740 A | 7/2000 | Kennedy |
| 5,874,046 A | 2/1999 | Megerle | 6,096,509 A | 8/2000 | Okun et al. |
| 5,876,675 A | 3/1999 | Kennedy | 6,100,541 A | 8/2000 | Nagle et al. |
| 5,880,071 A | 3/1999 | Parce et al. | 6,102,897 A | 8/2000 | Lang |
| 5,882,465 A | 3/1999 | McReynolds | 6,103,537 A | 8/2000 | Ullman et al. |
| 5,883,211 A | 3/1999 | Sassi et al. | 6,106,685 A | 8/2000 | McBride et al. |
| 5,885,432 A | 3/1999 | Hooper et al. | 6,110,343 A | 8/2000 | Ramsey et al. |
| 5,885,470 A | 3/1999 | Parce et al. | 6,123,205 A | 9/2000 | Dumitrescu et al. |
| 5,895,762 A | 4/1999 | Greenfield et al. | 6,123,798 A | 9/2000 | Gandhi et al. |
| 5,900,130 A | 5/1999 | Benregnu et al. | 6,130,098 A | 10/2000 | Handique et al. |
| 5,912,124 A | 6/1999 | Kumar | 6,132,580 A | 10/2000 | Mathies et al. |
| 5,912,134 A | 6/1999 | Shartle | 6,132,684 A | 10/2000 | Marino |
| 5,916,522 A | 6/1999 | Boyd et al. | 6,133,436 A | 10/2000 | Koster et al. |
| 5,916,776 A | 6/1999 | Kumar | D433,759 S | 11/2000 | Mathis et al. |
| 5,919,646 A | 7/1999 | Okun et al. | 6,143,250 A * | 11/2000 | Tajima ............................ 422/102 |
| 5,919,711 A | 7/1999 | Boyd et al. | 6,149,787 A | 11/2000 | Chow et al. |
| 5,922,591 A | 7/1999 | Anderson et al. | 6,156,199 A | 12/2000 | Zuk, Jr. |
| 5,927,547 A | 7/1999 | Papen et al. | 6,158,269 A | 12/2000 | Dorenkott et al. |
| 5,928,880 A | 7/1999 | Wilding et al. | 6,167,910 B1 | 1/2001 | Chow |
| 5,929,208 A | 7/1999 | Heller et al. | 6,168,948 B1 | 1/2001 | Anderson et al. |
| D413,391 S | 8/1999 | Lapeus et al. | 6,171,850 B1 | 1/2001 | Nagle et al. |
| 5,932,799 A | 8/1999 | Moles | 6,174,675 B1 | 1/2001 | Chow et al. |
| 5,935,401 A | 8/1999 | Amigo | D438,311 S | 2/2001 | Yamanishi et al. |
| 5,939,291 A | 8/1999 | Loewy et al. | 6,190,619 B1 * | 2/2001 | Kilcoin et al. ............... 422/916 |
| 5,942,443 A | 8/1999 | Parce et al. | D438,632 S | 3/2001 | Miller |
| D413,677 S | 9/1999 | Dumitrescu et al. | D438,633 S | 3/2001 | Miller |
| 5,948,227 A | 9/1999 | Dubrow | 6,197,595 B1 | 3/2001 | Anderson et al. |
| 5,955,028 A | 9/1999 | Chow | 6,211,989 B1 | 4/2001 | Wulf et al. |
| 5,955,029 A | 9/1999 | Wilding et al. | 6,213,151 B1 | 4/2001 | Jacobson et al. |
| 5,957,579 A | 9/1999 | Kopf-Sill et al. | 6,221,600 B1 | 4/2001 | MacLeod et al. |
| 5,958,203 A | 9/1999 | Parce et al. | 6,228,635 B1 | 5/2001 | Armstrong et al. |
| 5,958,694 A | 9/1999 | Nikiforov | 6,235,175 B1 | 5/2001 | Dubrow et al. |
| 5,959,221 A | 9/1999 | Boyd et al. | 6,235,313 B1 | 5/2001 | Mathiowitz et al. |
| 5,959,291 A | 9/1999 | Jensen | 6,235,471 B1 | 5/2001 | Knapp et al. |
| 5,964,995 A | 10/1999 | Nikiforov et al. | 6,236,581 B1 | 5/2001 | Foss et al. |
| 5,964,997 A | 10/1999 | McBride | 6,251,343 B1 | 6/2001 | Dubrow et al. |
| 5,965,001 A | 10/1999 | Chow et al. | 6,254,826 B1 | 7/2001 | Acosta et al. |
| 5,965,410 A | 10/1999 | Chow et al. | 6,259,635 B1 | 7/2001 | Torelli et al. |
| 5,965,886 A | 10/1999 | Sauer et al. | 6,261,431 B1 | 7/2001 | Mathies et al. |
| 5,972,187 A | 10/1999 | Parce et al. | 6,267,858 B1 | 7/2001 | Parce et al. |
| 5,973,138 A | 10/1999 | Collis | D446,306 S | 8/2001 | Ochi et al. |
| D417,009 S | 11/1999 | Boyd | 6,271,021 B1 | 8/2001 | Burns et al. |
| 5,976,336 A | 11/1999 | Dubrow et al. | 6,274,089 B1 | 8/2001 | Chow et al. |
| 5,980,704 A | 11/1999 | Cherukuri et al. | 6,280,967 B1 | 8/2001 | Ransom et al. |
| 5,980,719 A | 11/1999 | Cherukuri et al. | 6,281,008 B1 | 8/2001 | Komai et al. |
| 5,981,735 A | 11/1999 | Thatcher et al. | 6,284,113 B1 | 9/2001 | Bjornson et al. |
| 5,989,402 A | 11/1999 | Chow et al. | 6,287,254 B1 | 9/2001 | Dodds |
| 5,992,820 A | 11/1999 | Fare et al. | 6,287,774 B1 | 9/2001 | Kikiforov |
| 5,993,611 A | 11/1999 | Moroney, III et al. | 6,291,248 B1 | 9/2001 | Haj-Ahmad |
| 5,993,750 A | 11/1999 | Ghosh et al. | 6,294,063 B1 | 9/2001 | Becker et al. |
| 5,997,708 A | 12/1999 | Craig | 6,302,134 B1 | 10/2001 | Kellogg et al. |
| 6,001,229 A | 12/1999 | Ramsey | 6,302,304 B1 | 10/2001 | Spencer |
| 6,001,231 A | 12/1999 | Kopf-Sill | 6,303,343 B1 | 10/2001 | Kopf-sill |
| 6,001,307 A | 12/1999 | Naka et al. | 6,306,273 B1 | 10/2001 | Wainright et al. |
| 6,004,515 A | 12/1999 | Parce et al. | 6,306,590 B1 | 10/2001 | Mehta et al. |
| 6,007,690 A | 12/1999 | Nelson et al. | 6,319,469 B1 | 11/2001 | Mian et al. |

| | | |
|---|---|---|
| 6,322,683 B1 | 11/2001 | Wolk et al. |
| 6,326,083 B1 | 12/2001 | Yang et al. |
| 6,326,211 B1 | 12/2001 | Anderson et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | Mcreynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| D482,796 S | 11/2003 | Oyama et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,766,817 B2 | 7/2004 | da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | da Silva |
| D508,999 S | 8/2005 | Fanning et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,984,516 B2 | 1/2006 | Briscoe et al. |

| | | |
|---|---|---|
| D515,707 S | 2/2006 | Shinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | da Silva |
| 7,069,952 B1 | 7/2006 | Mcreynolds et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,910 B2 | 10/2006 | Unger et al. |
| 7,138,032 B2 | 11/2006 | Gandhi et al. |
| D534,280 S | 12/2006 | Gomm et al. |
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,618 B2 | 1/2007 | Skould |
| D537,951 S | 3/2007 | Okamoto et al. |
| D538,436 S | 3/2007 | Patadia et al. |
| 7,192,557 B2 | 3/2007 | Wu et al. |
| 7,195,986 B1 | 3/2007 | Bousse et al. |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,330 B2 | 10/2007 | Chow et al. |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Mehta |
| 7,527,769 B2 | 5/2009 | Bunch et al. |
| 7,553,671 B2 | 6/2009 | Sinclair et al. |
| D596,312 S | 7/2009 | Giraud et al. |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,704,735 B2 | 4/2010 | Facer et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| 7,867,776 B2 | 1/2011 | Kennedy et al. |
| 7,892,819 B2 | 2/2011 | Wilding et al. |
| 2001/0023848 A1 | 9/2001 | Gjerde et al. |
| 2001/0038450 A1 | 11/2001 | McCaffrey et al. |
| 2001/0046702 A1 | 11/2001 | Schembri |
| 2001/0055765 A1 | 12/2001 | O'Keefe et al. |
| 2002/0001848 A1 | 1/2002 | Bedingham et al. |
| 2002/0009015 A1 | 1/2002 | Laugharn, Jr. et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0060156 A1 | 5/2002 | Mathies et al. |
| 2002/0068357 A1 | 6/2002 | Mathies et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0169518 A1 | 11/2002 | Luoma et al. |
| 2002/0187557 A1 | 12/2002 | Hobbs et al. |
| 2003/0019522 A1 | 1/2003 | Parunak |
| 2003/0049833 A1 | 3/2003 | Chen et al. |
| 2003/0070677 A1 | 4/2003 | Handique et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0127327 A1 | 7/2003 | Kurnik |
| 2003/0136679 A1 | 7/2003 | Bohn et al. |
| 2003/0186295 A1 | 10/2003 | Colin et al. |
| 2003/0199081 A1 | 10/2003 | Wilding et al. |
| 2003/0211517 A1 | 11/2003 | Carulli et al. |
| 2004/0014238 A1 | 1/2004 | Krug et al. |
| 2004/0029258 A1 | 2/2004 | Heaney et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0072375 A1 | 4/2004 | Gjerde et al. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0240097 A1 | 12/2004 | Evans |
| 2005/0009174 A1 | 1/2005 | Nikiforov et al. |
| 2005/0048540 A1 | 3/2005 | Inami et al. |
| 2005/0084424 A1 | 4/2005 | Ganesan et al. |
| 2005/0106066 A1 | 5/2005 | Saltsman et al. |
| 2005/0121324 A1 | 6/2005 | Park et al. |
| 2005/0133370 A1 | 6/2005 | Park et al. |
| 2005/0135655 A1 | 6/2005 | Kopf-sill et al. |
| 2005/0152808 A1 | 7/2005 | Ganesan |
| 2005/0170362 A1 | 8/2005 | Wada et al. |
| 2005/0202470 A1 | 9/2005 | Sundberg et al. |
| 2005/0202504 A1 | 9/2005 | Anderson et al. |
| 2005/0208676 A1 | 9/2005 | Kahatt |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0272079 A1 | 12/2005 | Burns et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |

| | | |
|---|---|---|
| 2006/0165558 A1 | 7/2006 | Witty et al. |
| 2006/0165559 A1 | 7/2006 | Greenstein et al. |
| 2006/0166233 A1 | 7/2006 | Wu et al. |
| 2006/0177376 A1 | 8/2006 | Tomalia et al. |
| 2006/0183216 A1 | 8/2006 | Handique |
| 2006/0207944 A1 | 9/2006 | Siddiqi |
| 2006/0246493 A1 | 11/2006 | Jensen et al. |
| 2006/0246533 A1 | 11/2006 | Fathollahi et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0026421 A1 | 2/2007 | Sundberg et al. |
| 2007/0042441 A1 | 2/2007 | Masters et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0050804 A1 | 2/2008 | Handique et al. |
| 2008/0056948 A1 | 3/2008 | Dale et al. |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0182301 A1 | 7/2008 | Handique et al. |
| 2008/0192254 A1 | 8/2008 | Kim et al. |
| 2008/0247914 A1 | 10/2008 | Edens et al. |
| 2008/0262213 A1 | 10/2008 | Wu et al. |
| 2009/0047713 A1 | 2/2009 | Handique |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0136386 A1 | 5/2009 | Duffy et al. |
| 2009/0155123 A1 | 6/2009 | Williams et al. |
| 2009/0221059 A1 | 9/2009 | Handique et al. |
| 2009/0223925 A1 | 9/2009 | Morse et al. |
| 2010/0009351 A1 | 1/2010 | Brahmasandra et al. |

FOREIGN PATENT DOCUMENTS

| | | |
|---|---|---|
| DE | 19929734 | 12/1999 |
| EP | 0766256 | 4/1997 |
| FR | 2672301 | 8/1992 |
| FR | 2795426 | 12/2000 |
| JP | 58212921 A | 12/1983 |
| JP | H07-290706 | 11/1995 |
| JP | 2001-515216 | 9/2001 |
| JP | A-2001-527220 | 12/2001 |
| JP | A-2003-500674 | 1/2003 |
| JP | 2005-514718 | 5/2005 |
| JP | A-2005-204661 | 8/2005 |
| WO | WO 88/06633 | 9/1988 |
| WO | WO 92/05443 | 4/1992 |
| WO | WO 98/00231 | 1/1998 |
| WO | WO 98/22625 | 5/1998 |
| WO | WO 98/53311 | 11/1998 |
| WO | WO 99/01688 | 1/1999 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/078845 | 10/2002 |
| WO | WO 03/012325 | 2/2003 |
| WO | WO 03/012406 | 2/2003 |
| WO | WO 03/055605 | 7/2003 |
| WO | WO 2004/007081 | 1/2004 |
| WO | WO 2004/074848 | 9/2004 |
| WO | WO 2005/011867 | 2/2005 |
| WO | WO 2005/108620 | 11/2005 |
| WO | WO 2006/079082 | 7/2006 |
| WO | WO 2008/060604 | 5/2008 |
| WO | WO 2009/012185 | 1/2009 |

OTHER PUBLICATIONS

Handique et al., 2001, Mathematical modeling of drop mixing in a split-type microchannel, J. Micromech Microeng, 11:548-554.

International Search Report and Written Opinion dated Apr. 4, 2008 for PCT/US07/07513.

International Search Report and Written Opinion for PCT/US07/024022 dated Jan. 5, 2009.

Bollet, C. et al., "A simple method for the isolation of chromosomal DNA from Gram positive or acid-fast bacteria", Nucleic Acids Research, vol. 19, No. 8 (1991), p. 1955.

Breadmore, M.C. et al., "Microchip-Based Purification of DNA from Biological Samples", Anal. Chem., vol. 75 (2003), pp. 1880-1886.

Brody, et al., Diffusion-Based Extraction in a Microfabricated Device, Sensors and Actuators Elsevier, 1997, vol. A58, No. 1, pp. 13-18.

Broyles, et al., "Sample Filtration, Concentration, and Separation Integrated on Microfluidic Devices" Analytical Chemistry (American Chemical Society), vol. 75 No. 11: pp. 2761-2767.

Burns et al., "An Integrated Nanoliter DNA Analysis Device", Science 282:484-487 (1998).

Carlen et al., "Paraffin Actuated Surface Micromachined Valve," in IEEE MEMS 2000 Conference, p. 381-385, Miyazaki, Japan, Jan. 2000.

Chung, Y. et al., "Microfluidic chip for high efficiency DNA extraction", Miniaturisation for Chemistry, Biology & Bioengineering, vol. 4, No. 2 (Apr. 2004), pp. 141-147.

Handique K., et al., On-Chip Thermopneumatic Pressure for Discrete Drop Pumping, Analytical Chemistry, American Chemical Society, Apr. 15, 2001, vol. 73, No. 8, 1831-1838.

Handique, K. et al, "Microflidic flow control using selective hydrophobic patterning", SPIE, vol. 3224, pp. 185-194 (1997).

Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique, K. et al., "Mathematical Modeling of Drop Mixing in a Slit-Type Micochannel", J. Micromech. Microeng., 11:548-554 (2001).

Handique, K. et al., "Nanoliter Liquid Metering in Microchannels Using Hydrophobic Patterns", Anal. Chem., 72:4100-4109 (2000).

He, et al., Microfabricated Filters for Microfludic Analytical Systems, Analytical Chemistry, American Chemical Society, 1999, vol. 71, No. 7, pp. 1464-1468.

Ibrahim, et al., Real-Time Microchip PCR for Detecting Single-Base Differences in Viral and Human DNA, Analytical Chemistry, American Chemical Society, 1998, vol. 70, No. 9, pp. 2013-2017.

Khandurina, et al., Microfabricated Porous Membrane Structure for Sample Concentraction and Electrophoretic Analysis, Analytical Chemistry American Chemical Society, 1999, vol. 71, No. 9, pp. 1815-1819.

Kopp, et al., Chemical Amplification: Continuous-Flow PCR on a Chip, www.sciencemag.org, 1998, vol. 280, pp. 1046-1048.

Kutter, et al., Solid Phase Extraction on Microfludic Devices, J. Microcolumn Separations, John Wiley & Sons, Inc., 2000, vol. 12, No. 2, pp. 93-97.

Lagally, et al., Single-Molecule DNA Amplification and Analysis in an Integrated Microfluidic Device, Analytical Chemistry, American Chemical Society, 2001, vol. 73, No. 3 pp. 565-570.

Livache, T. et al., "Polypyrrole DNA chip on a Silicon Device: Example of Hepatitis C Virus Genotyping", Analytical Biochemistry, vol. 255 (1998), pp. 188-194.

Northrup, et al., A Miniature Analytical Instrument for Nucleic Acids Based on Micromachined Silicon Reaction Chambers, Analytical Chemistry, American Chemical Society, 1998, vol. 70, No. 5, pp. 918-922.

Oleschuk, et al., Trapping of Bead-Based Reagents within Microfluidic Systems,: On-Chip Solid-Phase Extraction and Electrochromatography, Analytical Chemical Society, 2000, vol. 72, No. 3, pp. 585-590.

Orchid BioSciences, Inc., www.orchid.com, Jul. 6, 2001.

Roche, et al. "Ectodermal commitment of insulin-producing cells derived from mouse embryonic stem cells" Faseb J (2005) 19: 1341-1343.

Ross, et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.

Shoffner, M. A. et al., Chip PCR.I. Surface Passivation of Microfabricated Silicon-Glass Chips for PCR, Nucleic Acids Research, Oxford University Press, 1996, vol. 24, No. 2, 375-379.

Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.

Waters, et al., Microchip Device for Cell Lysis, Multiplex PCR Amplification, and Electrophoretic Sizing, Analytical Chemistry, American Chemical Society, 1998, vol. 70, No. 1, pp. 158-162.

Weigl, et al., Microfluidic Diffusion-Based Separation and Detection, www.sciencemag.org, 1999, vol. 283, pp. 346-347.

Yoza, Brandon et al., DNA extraction using bacterial magnetic particles modified with hyperbranched polyamidoamine dendrimer, Mar. 20, 2003, vol. 101, No. 3, 219-228.

Yoza, et al., "Fully Automated DNA Extraction fro Blood Using Magnetic Particles Modified with a Hyperbranched Polyamidomine Dendrimer", Journal of Bioscience and Bioengineering, 95(1):21-26, 2003.

* cited by examiner

REAGENT TUBE

CROSS-REFERENCE TO RELATED APPLICATIONS

This application is a continuation of U.S. patent application Ser. No. 12/178,557, filed on Jul. 23, 2008 which is a continuation-in-part of each of U.S. patent application Ser. No. 12/218,498, filed on Jul. 14, 2008, U.S. patent application Ser. No. 12/218,416, filed on Jul. 14, 2008, and U.S. patent application Ser. No. 12/173,023, filed Jul. 14, 2008, each of which claims the benefit of priority to U.S. provisional Patent Application Ser. No. 60/959,437, filed Jul. 13, 2007. All of the above patent applications are incorporated herein by reference in their entireties.

BACKGROUND OF THE INVENTION

1. Field of the Invention

The technology described herein generally relates to reagent tubes designed to facilitate pipetting of small volumes of liquid from within, and more particularly to reagent tubes that are used in extracting microfluidic quantities of polynucleotides in solution following extraction from biological samples.

2. Description of the Related Art

The medical diagnostics industry is a critical element of today's healthcare infrastructure. At present, however, diagnostic analyses no matter how routine have become a bottleneck in patient care. There are several reasons for this. For example, many diagnostic analyses can only be done with highly specialist equipment that is both expensive and only operable by trained clinicians. Such equipment is found in only a few locations, and often there is just one in any given urban area. This means that most hospitals are required to send out samples for analyses to these locations, thereby incurring shipping costs and transportation delays, and possibly even sample loss or mishandling.

Understanding that sample flow breaks down into several key steps, it would be desirable to consider ways to automate or make efficient as many of these as possible. In one key step, a biological sample, once extracted from a patient, must be put in a form suitable for a processing and detection regime that typically involves using PCR to amplify a vector of interest. Once amplified, the presence or absence of the vector in the sample needs to be determined unambiguously. Preparing samples for PCR is currently a time-consuming and labor intensive step, though not one requiring specialist skills, and could usefully be automated. By contrast, steps such as PCR and nucleotide detection have customarily only been within the compass of specially trained individuals having access to specialist equipment.

Sample preparation is labor intensive in part because of the number of reagents required, and the need for multiple liquid transfer (e.g., pipetting) operations. Furthermore, a trend towards portable diagnostic instruments, or those that can be easily installed in almost any healthcare setting (without requiring a dedicated facility), has meant that the instruments are configured to analyze very small (microfluidic or smaller) volumes of polynucleotide-containing solutions. With such volumes, it becomes important to minimize sample loss— such as from liquid transfer operations—during sample preparation. Even a loss of a very small fraction of a processing volume could result in loss of a significant number of copies of target polynucleotide and thereby result in a concomitant loss of amplification and detection sensitivity and— potentially—a false negative diagnosis. A major source of loss of liquid samples and solutions is from incomplete pipetting, where a pipette attempts to suck an entire quantity of fluid from a container, but where some fraction of that quantity is retained in the container, such as on the interior surfaces.

Various interior surface features in reagent tubes have been described elsewhere. U.S. Pat. No. 4,466,740 describes an array of reaction vessels on a plate, wherein each vessel has a conical interior lower surface that is stepped so that a number of concentric ridges of increasing diameter span between the bottom of the vessel and the vessel at its maximum width. Such a shape of interior surface is likely to present an increased surface area on which solution may remain during pipetting, and are unlikely to effectively channel the solution towards the location of a pipette tip. U.S. Pat. No. 6,143,250 (the '250 patent) describes liquid storage vessels having "ditches" in their lower interior surfaces that follow the interior surface of an inclined edge of the vessel. Although the '250 patent suggests that these grooves can be present in numbers of greater than two, and arranged radially with respect to the center of the vessel, such a configuration has at least the drawback that it would require a complex manufacture of the vessel, and are therefore limited to particular vessels, not necessarily those that are used in routine laboratory processes, such as biological sample preparation.

There is therefore a need for a method and apparatus of carrying out sample preparation on samples, so that loss of liquid volumes during liquid transfer is reduced. Such methods and apparatus could also find application to liquid transfer operations used in other fields, where mitigation of sample loss during work-up is important.

The discussion of the background herein is included to explain the context of the inventions described herein. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY OF THE INVENTION

The technology described herein includes a reagent tube comprising a pattern of ridges extending radially and centered at the bottom of the interior surface of the tube. Also contemplated are radially oriented patterns of grooves on the bottom interior surface of the tube.

The reagent tube described herein typically comprises a wall having an upper portion, usually cylindrical, and a lower portion, usually conical or tapering towards a bottom, and has an exterior surface and an interior surface. The pattern of ridges is typically star-shaped and is disposed on the interior surface of the tube, at the bottom of the tube.

The technology described herein further includes methods of using a reagent tube, as described herein, such as a method of removing all, or substantially all, of a liquid from the tube by use of a pipette tip. The pipette tip may be removably attached to a manually, such as hand-operated, pipette, or may be removably attached to an automatic dispensing apparatus.

The reagent tube herein typically finds use in sample preparation, that sequence of processing steps by which polynucleotide molecules, such as DNA and/or RNA, present in a biological sample (such as blood, sputum, semen, or urine), are extracted from their cellular matrix, and placed in a form suitable for amplification, such as by PCR, and subsequent detection as part of a diagnostic test.

DETAILED DESCRIPTION OF THE INVENTION

Reagent Tubes

The reagent tubes described herein are designed to facilitate pipetting of small volumes of liquid from within, such as to transfer the liquid to another container, with very little attendant loss of liquid.

The reagent tubes can be used in extracting microfluidic quantities of polynucleotides in solution following isolation of such polynucleotides from biological samples, such as in conjunction with a holder of various reagents as described in U.S. Patent Publication. No. 2009-0129978 A1, filed by ExpressMail on Jul. 14, 2008 (and entitled "Reagent Holder, and Kits Containing Same", in the name of Wilson, et al.), and an automated pipette head and dispenser as described in U.S. Patent Publication No. 2009-0130745 A1, filed by ExpressMail on Jul. 14, 2008 (and entitled "Integrated Apparatus for Performing Nucleic Acid Extraction and Diagnostic Testing on Multiple Biological Samples", in the name of Williams, et al.), both of which are incorporated herein by reference. Exemplary procedures for sample preparation from polynucleotide-containing biological samples are found in U.S. Patent Publication Nos. 2010-0009351 A1, and 2009-0131650 A1, both filed Jul. 11, 2008, and incorporated herein by reference.

However, reagent tubes consistent with the embodiments described herein are not exclusively for use with automated pipetting apparatus but also can be used in conjunction with manual processing, such as pipetting by hand.

Tubes consistent with the embodiments herein may have a variety of volumes, typically in the range 0.1 ml to 0.65 ml, such as 03 ml, 0.6 ml, or in the range 1.5-2.0 ml, or may have intermediate, or greater, volumes than those specifically delimited. They may also have a variety of shapes such as conical, barrel-shaped (wider at a middle portion than at top and bottom portions), or cylindrical with a tapered or conical bottom. Usually, reagent tubes are circular in cross-section, but other cross sections are possible and consistent herewith, and include but are not limited to: rectilinear, such as square or rectangular, like a cuvette; polygonal, such as pentagonal or hexagonal; and oval. Ordinarily, the tubes have a unitary construction, though in certain instances may be constructed from two or more parts fused or otherwise joined together as applicable. Typically, the tubes are configured to accept a pipette tip for deposit and/or retrieval of fluids.

The features of the reagent tubes as described herein may be found in or on the interior surfaces of many fluid containing vessels, including, but not limited to: vessels configured to carry out reactions, such as PCR tubes; arrays, such as microarray plates, having many vessels arranged in a single substrate; snap-in tubes, such as tubes that contain reagents and are shipped separately or loosely, but when used are snapped into a supporting member such as a rack or a holder; disposable tubes; re-usable tubes; tubes that are sealed to limit contact of their contents with air and/or moisture during storage or transport; tubes that are sealable and re-sealable, such as having a removable, or flip-up cap; tubes that can be labeled for a single use, or labeled for multiple uses; tubes that are made of a clear, or a translucent, or an opaque material, depending upon, e.g., photosensitivity of the contents; tubes that contain liquid reagents such as those that are directly pipetted out of the tubes; and tubes that contain solid, e.g., particulate, or lyophilized, reagents that are constituted into liquid form prior to pipetting, such as by dissolving upon contact with a liquid such as an aqueous buffer solution; and tubes that are made of plastic, or glass, or quartz.

As described elsewhere herein, the reagent tubes are configured to have a star-shaped—also referred to as stellated—pattern (see FIGS. 1A and 1B) on their bottom interior surfaces. Still other tubes for uses referenced herein, as well as for other uses not herein described, can be similarly configured.

Figure 3:
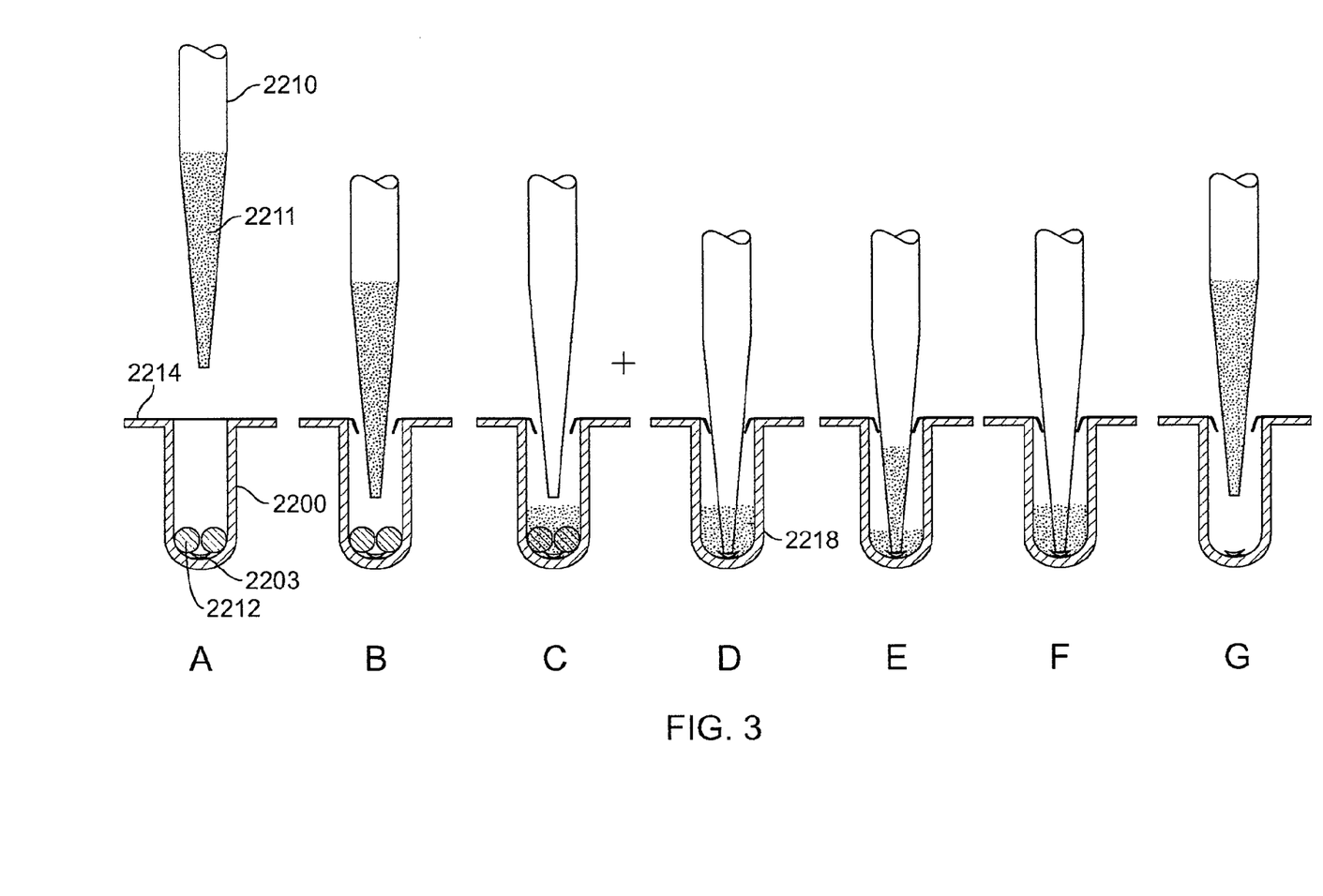
FIG. 3 shows a sequence of pipetting operations in conjunction with a reagent tube having a stellated feature.

The design of the star shaped pattern is important, especially when present in a reagent tube used for recovery of DNA or RNA present in very small quantities (low copy numbers) in a clinical sample, or an extract therefrom. The star-shaped pattern ensures that when a fluid is withdrawn from the tube, a pipette tip can be bottomed out in the tube and still be able to withdraw the entire, or almost the entire fluid from the tube, as shown in FIG. 3, further described herein. This is important because, when working with such small volumes, and when target DNA can be present in very few copies, sample loss due to imperfections of pipetting is to be minimized to every extent possible. Additionally, the stellated pattern should be designed to minimize surface area as well as dead-end grooves that tend to have two undesirable effects: to trap liquid, and to increase undesirable retention of molecules such as polynucleotides by adsorption.

Accordingly, the stellated pattern should enable pipetting of most of the liquid (residual volume<1 microliter) when used with a pipette bottomed out with the bottom of the tube. Although it is not necessary for a pipette tip to bottom out in the reagent tubes described herein, an advantage of it so doing is that a very clear indication of the position of the tip during pipetting is obtained and thereby a consistent positioning can be accomplished across multiple pipetting operations. A requirement that a pipette tip be positioned at some intermediate distance above the bottom of the tube in order to maximize pipetting efficiency, would be harder to verify and to make consistent and reproducible over large numbers of operations even when using an automated pipetting device.

The design of the stellated or star-shaped pattern can be optimized to maximize the flow rate of liquid through various gaps in the pattern that lie between a bottomed out pipette, such as a p1000 pipette, and the star pattern. It would be understood that, although the description herein pertains to pipettes and pipette tips typically used in sample preparation of biological samples, the principles and detailed aspects of the design are as applicable to other types of pipette and pipette tip, and may be so-adapted.

Figure 1A:
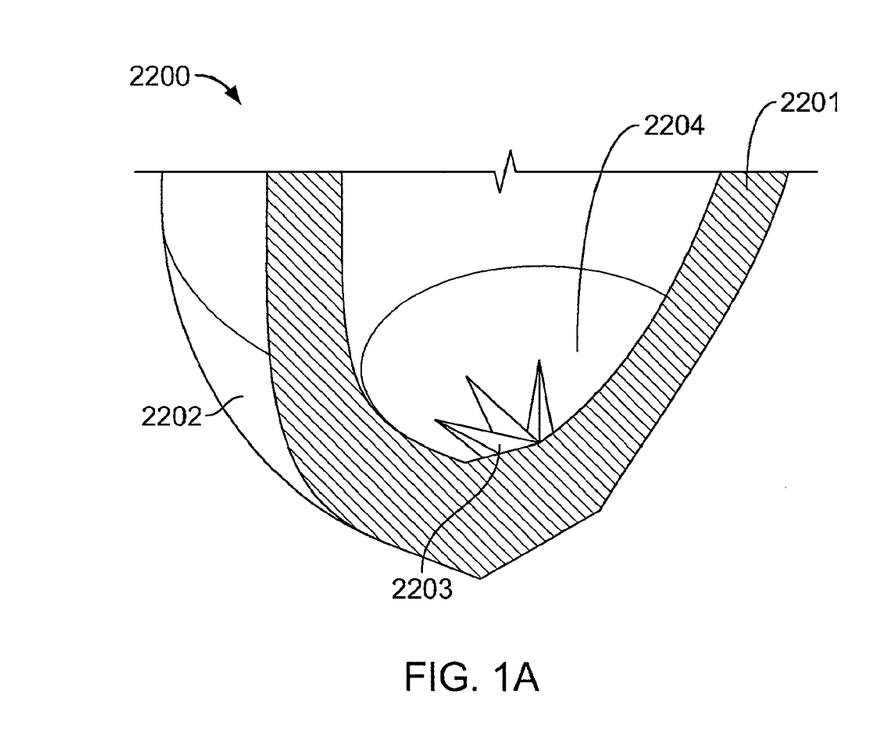
FIGS. 1A and 1B show a stellated feature on the interior of a reagent tube, in cross-sectional (FIG. 1A) and top plan (FIG. 1B) views.

FIG. 1A shows a cross sectional perspective view of a reagent tube 2200 having side wall 2201 and bottom portion 2202. Interior surface 2204 of the bottom portion is visible. An exemplary star-shaped feature 2203 is shown in part, as three apical portions, which may be grooves or may be ridges raised above the lower interior surface 2204. Typically, however, the star-shaped pattern is present as a raised portion on the lower interior surface of the tube.

Figure 1B:
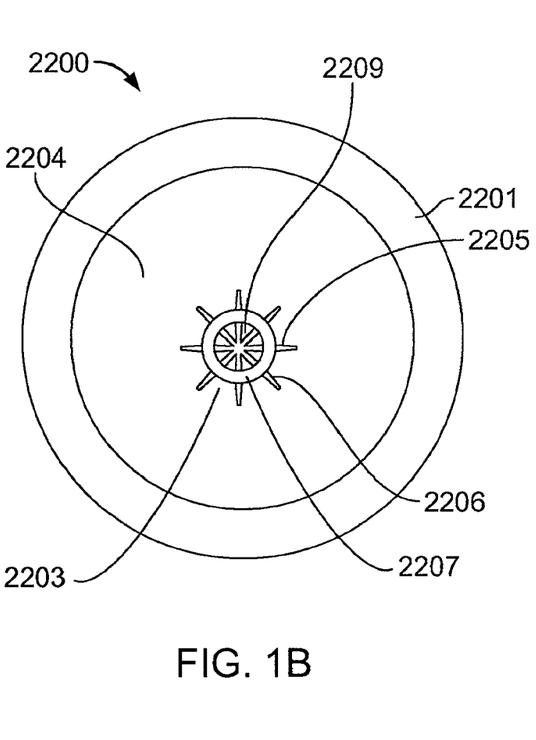

FIG. 1B shows a plan view of the reagent tube of FIG. 1A, looking down its central axis from the top. Thus wall 2201 in FIG. 1B is shown at its widest diameter, typically corresponding to the top of tube 2200. The exemplary star pattern 2203 shown in FIG. 1B in plan view resembles a "ship's wheel" and comprises a center 2209, a circular ring 2207 centered on center 2209, and eight radial segments 2205 configured as radial ridges or grooves. Each radial segment meets the other radial segment at center 2209, and has a radial end 2206, also referred to as an apex or vertex. Star pattern 2203 in FIG. 1B has eight radial segments, but it would be understood that a star pattern having fewer or a greater number of radial segments, such as 3, 4, 5, 6, 7, 9, 10, or 12, would be consistent with the design herein. The number of radial segments of the star should be a minimum consistent with effective liquid pipetting and ease of manufacture. The radial segments should also be spaced apart enough not to trap the tip of any of the pipette tips to be used in the various liquid handling applications.

Center 2209 is typically positioned coincidentally with the geometric center of the bottom of reagent tube 2200. Such a tube is typically circular in cross-section, so that identifying its geometric center (e.g., at a crossing point of two diameters) is normally straightforward. Center 2209 may be larger than shown in FIG. 1B, such as may be a circular cutout or raised portion that exceeds in diameter the region formed by the meeting point of radial segments 2205.

Ring 2207 is an optional feature of star-shaped pattern 2203. Typically ring 2207 is centered on center 2209, and typically it also has a dimension that corresponds to the lower surface or caliber of a pipette tip. Thus, when a pipette tip 'bottoms out' in the bottom of reagent tube 2200, the bottom of the pipette tip rests in contact with ring 2207. Ring 2207 is thus preferably a cut-out or recessed feature that can accommodate the pipette tip and assist in guiding its positioning centrally at the bottom of the tube. Ring 2207 may alternately be a raised or ridge-like feature, according to manufacturing or other preference. In other embodiments more than one, such as 2, 3, or 4, concentric rings 2207 are present, so that pipette tips of varying calibers can be used with the same reagent tube, and each can be suitably positioned, while pipetting, in contact with one of the respective rings.

In the embodiment shown in FIG. 1B, the segments are narrower (occupy a smaller radial angle) than the gaps between them. In other embodiments, the radial segments may be proportionately wider than the gaps between them. When configured as grooves, radial segments 2205 are separated by ridges (occupying the space in between adjacent grooves). In other embodiments, the grooves and ridges that separate them are of equal widths at each radial distance from the center. It may be more appropriate to describe the stellated features as having ridges or • grooves, depending on which occupies the cumulative greater spatial extent.

Figure 2A:
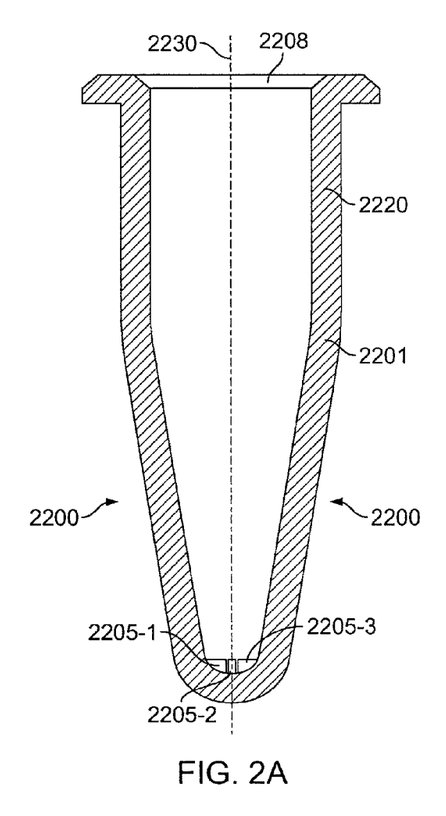
FIGS. 2A, 2B, and 2C show a stellated feature on the interior of a reagent tube, in cross-sectional plan (FIG. 2A), top plan (FIG. 2B), and close-up (FIG. 2C) views.
Figure 2B:
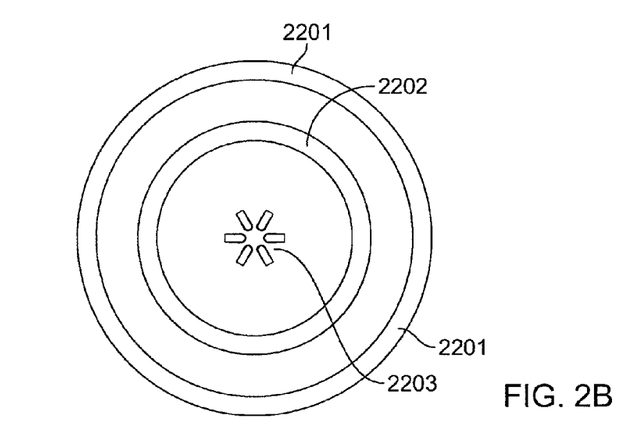

FIG. 2A shows in cross-sectional plan view a reagent tube 2200 having another exemplary stellated feature 2203, wall 2201, and sealed top 2208. The tube has a cylindrical upper portion 2220, and a tapering lower portion 2202. Shown as a dashed line 2230 in FIG. 2A is a central axis of symmetry of the tube, about which the tube is rotationally symmetric. FIG. 2B shows a top plan view of the reagent tube in FIG. 2A looking down its central axis towards stellated feature 2203 centered at the bottom of the tube. The ring denoted 2202 in FIG. 2B denotes an intermediate diameter of lower portion 2202. Stellated feature 2203 is shown in further detail in FIG. 2C as having 6 radial segments, three adjacent ones of which are labeled 2205-1, 2205-2, and 2205-3, respectively. The axis labeled X-X' corresponds to the viewpoint looking into the plane of the page in FIG. 2A. Thus, segment 2205-2 is shown as being in the middle of the stellated feature, and segments 2205-1 and 2205-3 are shown in cross-section, in FIG. 2A.

Figure 2C:
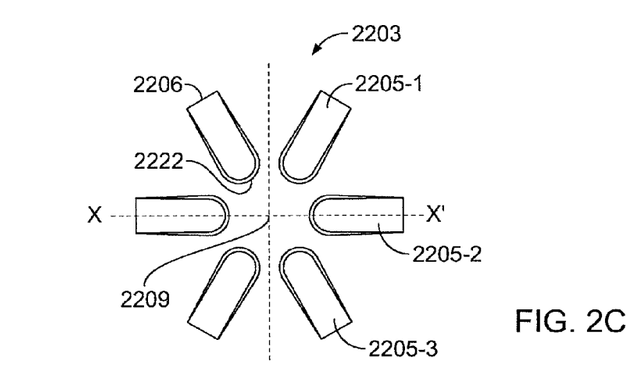

Characteristic features of the stellated pattern in FIGS. 2A-C include the following: segments 2205 may be configured as grooves or as ridges but are typically ridges, as shown in FIG. 2A; segments 2205 do not meet at center 2209 of the stellated pattern so that, where segments 2205 are ridges, a pipette tip that rests thereupon when pipetting is resting above a space at center 2209; there is no ring corresponding to ring 2207 in FIG. 1B; apices 2206 of segments 2205 are squared off but may be rounded in shape, or may be pointed; segments 2205 have interior apices 2222 that are also rounded, but may be pointed or squared off; and segments 2205 have, in cross-sectional view, rounded or flat bottoms if grooves, or rounded or flat upper surfaces if ridges; segments 2205 may be beveled so that they are narrower in their upper portion than at their lower portion, if ridges, or so that they are narrower in their lower portion than at their upper portion, if grooves.

A star pattern 2203 as described herein is configured to have dimensions that give an optimal flow-rate of liquid out of the reagent tube into a suitably positioned, such as a bottomed-out, pipette tip. The star pattern in FIGS. 1B and 2B is shown as being significantly smaller in diameter than the diameter of the tube at its widest point. The star pattern may have, in various embodiments, a diameter (measured from center 2209 to apex 2206 of a ridge or groove 2205) that is from 1-10%, or from 5-20%, or from 10-25%, or from 15-30%, or from 20-40%, or from 25-50%, or from 30-50%, or from 40-60%, or from 50-75%, or from 65-90% of the maximum diameter of the reagent tube.

The radial segments are typically rounded in their lower surfaces, such as semi-circular in cross section, or having a curved surface that is in cross section an arc of a circle, ellipse, parabola, or hyperbola, but may also be V-shaped. The segments may also be trapezoid in cross-section, such as having a wider upper portion than the bottom, which is flat, the upper portion and the bottom being connected by sloping walls.

In some embodiments, for ease of manufacture, the radial segments end on the same level as one another in the bottom of the tube. Thus the apices 2206 are all disposed on the circumference of a circle whose plane lies perpendicular to the cylindrical axis of the tube. In other embodiments, the segments do not all end on the same level. For example, apices 2206 may alternately be on different levels, and thus the apices are alternately disposed on the respective circumferences of two concentric circles that occupy different, parallel, planes in space from one another.

Radial segments 2205 are shown in FIGS. 1B and 2C as having equal lengths (as measured from center 2209 to apex 2206). This need not be so. In alternative embodiments, segments may have different lengths from one another, for example, as alternating lengths on alternating segments, where there are an even number of segments. Furthermore, apices 2206 may be rounded, rather than pointed, or may be squared off. Typically radial segments 2205 each have a length that is longer than the radius of the inlet hole in the largest pipette tip that is used in connection therewith. Typically radial segments 2205 have a width that is narrower than the diameter of the inlet hole in the largest pipette tip that is used in connection therewith, but it need not be the case.

Typically the radial segments taper uniformly in width and height or depth from center 2209 to each respective apex 2206. Still other configurations are possible, such as a segment that follows a constant width, or depth, out to a particular radial extent, within 30-60% of its length such as near its midpoint of length, and then narrows and/or becomes shallower towards its apex 2206. Alternatively, a radial segment may start narrow at center 2209, widen to a widest region within 30-60% of its length, such as near its midpoint of length, and then narrow towards its apex. Still other possibilities, not described herein, are consistent with the stellated pattern of the reagent tubes herein.

In a 0.3 ml tube, the radius of the star-pattern formed from the radial segments, measured as the shortest distance from center 2209 to an apex 2206, is typically around 0.5 mm, but may be from 0.1-1 mm, or from 0.3-0.7 mm, or from 0.5 to 1.5 mm, or from 0.7 to 2 mm.

In a 0.3 ml tube, the width of each radial segment 2205 at its widest point is typically around 50 microns, and the width typically tapers uniformly from a widest point, closest to or at center 2209, to a narrower width at the apex 2206.

In a 0.3 ml tube, the height (for a ridge) or depth (for a groove) of a segment at the deepest point is typically around 25-50 microns and the height depth typically tapers uniformly from a highest or deepest point respectively, closest to or at center 2209, to an apex 2206.

In another embodiment, in a 0.3 ml tube, the radial segments should be rounded off and less than 100 microns deep (or high), or less than 50 microns deep (or high), or less than 25 microns deep (or high).

The stellated pattern typically has a rotation axis of symmetry, the axis disposed perpendicular to the bottom of the tube and through center 2209 (concentric with a cylindrical axis of the tube), so that the radial segments are disposed symmetrically about the rotation axis. By this is meant that, for n segments, a rotation by an angle of 2π/n about the central (rotational) axis can bring each segment into coincidence with the segment adjacent to it.

The stellated shapes shown in FIGS. 1B and 2B, 2C are not limiting in that they comprise a center, a number of radial segments 2205, and an optional circular ring 2207. Other star-shaped geometries may be used, and, depending upon ease of manufacture and efficacy of use, may be preferred. For example, a star-shaped pattern can be created simply be superimposing two or more polygons having a common center, but offset rotationally with respect to one another by a rotation about the central axis. (See, for example "star polygons" described at the world wide web site mathworld.wolfram.com/StarPolygon.html.) Such alternative manners of creating star-shaped patterns are utilizable herein.

Also shown in the side plan view of FIG. 2A is a top 2208 of tube 2200. Top 2208 is typically made of aluminum foil, which may be heat-sealed on to the top of the tube. Although other layers, or a combination of layers, such as a laminate layer, as further described in U.S. Patent Publication. No. 2009-0129978A1, filed by ExpressMail on Jul. 14, 2008 (and entitled "Reagent Holder, and Kits Containing Same", can be placed on top of the reagent tube to seal it, typically a layer of aluminum foil is adequate, where the tube contents are solid, e.g., lyophilized, reagents. In some embodiments, the top of the reagent tube has chamfer edges to reduce expansion of the top rim of the tube during heat sealing of a foil on the top of the tube.

The reagent tube described herein may further comprise an identifiable code, such as a 1-D or a 2-D bar-code on the top 2208. Such a code is useful for identifying the composition of the reagents stored within, and/or a batch number for the preparation thereof, and/or an expiry date. The code may be printed on with, for example, an inkjet or transfer printer. The code may also be attached, or affixed, or printed on, the side of the tube, such as on an exterior surface of wall 2201.

Exemplary Manufacture

A stellated feature such as described herein may be positioned on the interior surface of the bottom of a reagent tube during manufacture of the tube by, for example injection moulding. The stellated feature is typically constructed as a raised feature, proud from the bottom interior surface. Thus, during manufacture of a reagent tube described herein by injection moulding, an outer portion of the mould is a cavity defining the exterior shape of the tube. An interior shape of the tube is formed by an inner portion of the mould positioned concentrically with the outer portion of the mould, and having a star-shaped structure milled out of its tip. Thus, when liquid plastic is injected into the space between the inner and the outer portions of the mould, the star-shape is formed as a raised portion on the bottom interior surface of the tube that is so-formed. Alternately, if the stellated feature is constructed as a recessed feature, the interior portion of the mould will have a complementary stellated feature projecting from its bottom surface.

Reagent tubes may be manufactured by injection moulding in batches, such as via an array of tube-shaped moulds in a single substrate. Tubes made in batch in this way may be imprinted with a non-functional marking characteristic of the location in the array, for example, for purposes of quality control.

Exemplary Pipetting Operations

FIG. 3 has a number of panels, A-G, each representing, in sequence, a stage in a pipetting operation carried out in conjunction with a reagent tube 2200 having a stellated pattern 2203, shown in cross section on the bottom interior surface of the tube 2200 and as further described herein. FIG. 3 is now described, as follows.

At A, a pipette tip 2210, containing a liquid 2211 (such as a buffer solution), is positioned directly or approximately above the center of reagent tube 2200. The tube contains a number of lyophilized pellets 2212, and is sealed by a layer 2214, such as of foil, as further described herein.

At B, the pipette tip is lowered, piercing seal 2214, and brought into a position above the particles 2212.

At C the liquid 2211 is discharged from the pipette tip on to the particles, dissolving the same, as shown at D. After the particles are fully dissolved, forming a solution 2218, the pipette tip is lowered to a position where it is in contact with the stellated pattern 2203.

At E, the pipette tip is caused to suck up the solution 2218 (typically leaving less than 1 µl of solution 2218 in the tube), and at F, the tip may optionally discharge the solution back into the tube. Steps E and F may be repeated, as desired, to facilitate dissolution and mixing of the lyophilized components into solution.

At G, after sucking up as much of the solution 2218 as is practicable into the pipette tip, the pipette tip is withdrawn from the tube. Ideally, 100% by volume of the solution 2218 is drawn up into the pipette tip at G. In other embodiments, and depending upon the nature of solution 2218, at least 99% by volume of the solution is drawn up. In still other embodiments, at least 98%, at least 97%, at least 96%, at least 95%, and at least 90% by volume of the solution is drawn up.

The following examples illustrate an embodiment of the invention described and claimed herein, and are not intended to be limiting.

EXAMPLES

Example 1

Reagent Tube

An exemplary reagent tube, showing various dimensions, is shown in FIGS. 4A-4D. Tolerances on the shown dimensions, during manufacture, are as follows: features≦0.5 inches are machined to within±0.010 inches; features<0.5 inches are machined to within±0.005 inches; feature locations, such as theoretical center points and theoretical center lines, are within±0.010 inches of those shown in the drawings. It is to be understood that dimensions can also be represented in their metric system equivalents without departing from the scope of the technology herein.

Figures 4A, 4B:
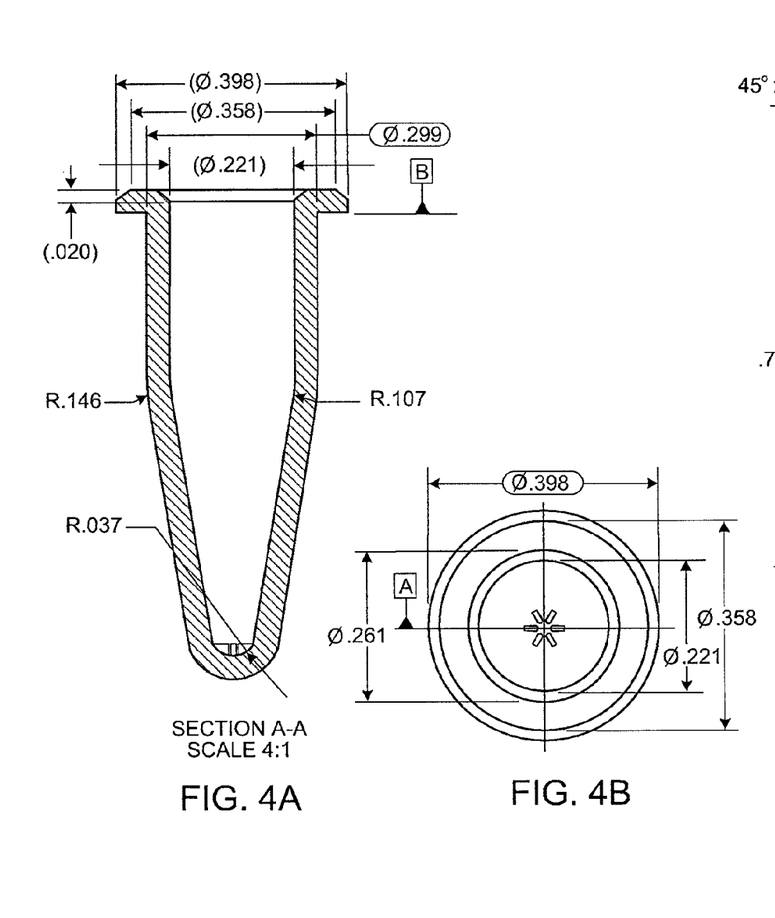
FIGS. 4A, 4B, 4C, and 4D show an embodiment of a reagent tube having a stellated feature as further described herein, in cross-sectional (FIG. 4A), top plan (FIG. 4B), side plan (FIG. 4C), and close-up (FIG. 4D) views.
Figure 4C:
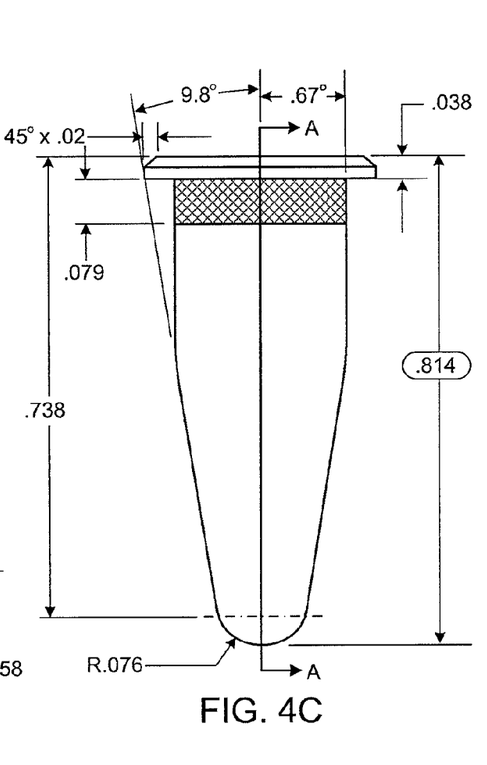

The cross-hatch area shown on the upper portion of the tube in FIG. 4C is an area on which a marking may be made, such as during manufacture, for the purpose of indicating product origin, identifying the batch, or for quality control.

Figure 4D:
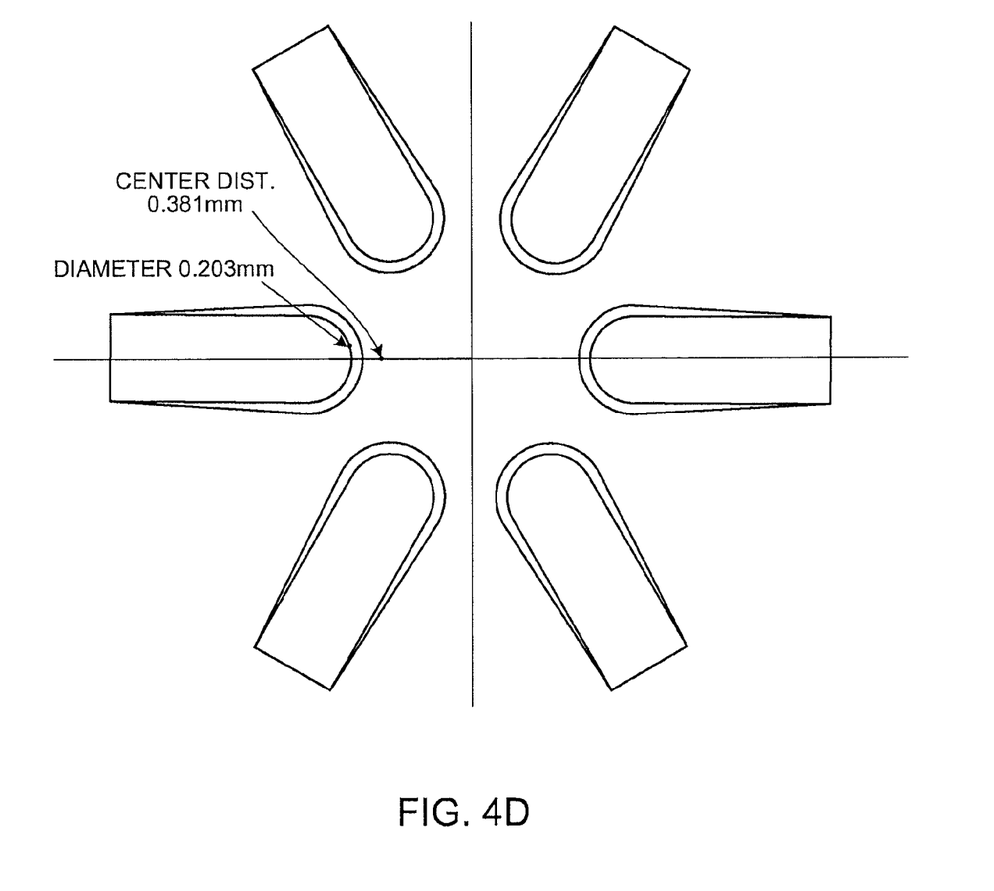

The pattern of ridges shown in FIG. 4D is such that each ridge comprise a rectangular portion capped by a semi-circular arc, the semi-circular arc being disposed close to the common center of the pattern of ridges and having a diameter of 0.203 mm. In the embodiment shown in FIG. 4D, the distance from the center of the circle of which the semi-circular arc is formed to the center of the pattern is 0.381 mm.

The tube is made from polypropylene homopolymer, e.g., available from Cannel Olefins Ltd., and identified as product no. Capilene U77 AV (see, e.g., world wide web site carmelolefins.co.il/Media/Uploads/Capilene_nomenclatur.pdf).

Surfaces are SPI (Society of the Plastics Industry) grade A-2, a known surface quality measurement, or better.

Any and all flashes and burrs resulting from the manufacture are removed and, in order to be used, the tube should not come into contact with grease, dust, mold release or other foreign substances. The tube should also be free of cracks, crazing, scratches, and internal defects or particulates obvious to the unaided eye.

Example 2

Foil Piercing and Dissolution of Lyophilized Reagents

The containers of lyophilized reagents provided in conjunction with a holder as described herein are typically sealed by a non-plasticized aluminum foil. Aluminum foil bursts into an irregular polygonal pattern when pierced through a pipette and leaves an air vent even though the pipette is moved to the bottom of the tube. In order to save on reagents, it is desirable to dissolve the reagents and maximize the amount withdrawn from the tube. To accomplish this, a ridged-star (stellated) pattern is placed at the bottom of the container to maximize liquid volume withdrawn, and flow velocity in between the ridges.

Exemplary steps for dissolving solid particles, and withdrawing fluid are as follows:

1. Pierce through the pipette and dispense the fluid away from the lyophilized material. If the pipette goes below the level of the lyophilized material, it will go into the pipette and may cause jamming of the liquid flow out of the pipette.
2. Let the lyophilized material dissolve for a few seconds.
3. Move pipette down touching the ridged-bottom of the tube.
4. Perform an adequate number of suck and spit operations (4-10) to thoroughly mix the reagents with the liquid buffer.
5. Withdraw all the reagents and move pipette to dispense it into the next processing tube.

The foregoing description is intended to illustrate various aspects of the present inventions. It is not intended that the examples presented herein limit the scope of the present inventions. The technology now being fully described, it will be apparent to one of ordinary skill in the art that many changes and modifications can be made thereto without departing from the spirit or scope of the appended claims.

What is claimed is:

1. A reagent tube for insertion into a tube holder strip, comprising:
    a tube body having a top, a bottom, and an interior surface, wherein the top, bottom, and interior surface of the tube body define a volume configured to hold a liquid;
    a radially-extending lip at the top of the tube body configured for locking engagement with cooperating structure on a tube holder strip to retain the tube after insertion into a tube holder strip;
    a pattern of convex ridges extending radially and centered at the bottom of the interior surface of the tube, wherein the convex ridges extend vertically from the bottom interior surface of the tube body, wherein the pattern of ridges and the ridges are configured to enable pipetting of substantially all of the liquid held in the reagent tube; and
    a ring centered at the bottom of the interior surface of the tube, wherein the pattern of radially extending convex ridges intersect the ring.

2. The tube of claim 1, wherein the number of ridges is selected from 3, 4, 5, 6, 8, 9, 10, or 12.

3. The tube of claim 1, wherein the ridges do not meet one another at a center of the pattern.

4. The tube of claim 1, wherein each of the ridges has a width, wherein the width tapers from a widest point to an apex.

5. The tube of claim 4, wherein the widest point has a width of 50 microns.

6. The tube of claim 1, wherein each of the ridges has a height, wherein the height tapers from a highest point to an apex.

7. The tube of claim 1, wherein each of the ridges has a length, measured as the shortest distance from its widest point to its apex.

8. The tube of claim 6, wherein the length is 0.5 mm.

9. The tube of claim 1, having a volume of 0.3 ml.

10. The tube of claim 1, having a volume of between 0.1 ml to 0.65 ml.

11. The reagent tube of claim 1, where the top of the reagent tube has chamfer edges to reduce expansion of the top rim of the tube during heat sealing of a foil on the top of the tube.

12. The reagent tube of claim 1, further comprising a reagent contained therein, and wherein the tube is sealed on top by a foil.

13. The reagent tube of claim 12, further comprising an identifiable code on the top.

14. The reagent tube of claim 12, wherein the reagent is in liquid or lyophilized form.

15. The tube of claim 1, wherein the pattern of ridges extending radially and centered at the bottom of the interior surface of the tube is a stellated pattern.

16. The tube of claim 15, wherein each of the ridges has a width, wherein the width tapers from a widest point to an apex.

17. The tube of claim 15, wherein each of the ridges has a height, wherein the height tapers from a widest point to an apex.

18. The tube of claim 15, wherein the stellated pattern has a rotation axis of symmetry, the axis disposed perpendicular to the bottom of the tube, and wherein the ridges are disposed symmetrically about the rotation axis.

19. The tube of claim 15, wherein the stellated pattern additionally comprises a circular cutout at the center of the bottom of the tube.

20. The reagent tube of claim 15, wherein the stellated pattern is designed to enable liquid to be pipetted out of the tube, with less than 1 microliter of residual volume.

21. The tube of claim 16, wherein the widest point is closest to a center of the stellated pattern.

22. The tube of claim 17, wherein the highest point is closest to a center of the stellated pattern.

23. The tube of claim 22, wherein the highest point has a height of 25-30 microns.

24. A reagent holding system, comprising:
a reagent tube, comprising:
a tube body having a top, a bottom, and an interior surface, wherein the top, bottom, and interior surface of the tube body define a volume configured to hold a liquid;
a radially-extending lip at the top of the tube body;
a pattern of convex ridges extending radially and centered at the bottom of the interior surface of the tube, wherein the convex ridges extend vertically from the bottom interior surface of the tube body, wherein the pattern of ridges and the ridges are configured to enable pipetting of substantially all of the liquid held in the reagent tube; and
a ring centered at the bottom of the interior surface of the tube, wherein the pattern of radially extending convex ridges intersect the ring; and
a tube-holding strip having an opening for receiving the reagent tube with a cooperating structure configured for locking engagement with the lip of the tube body after insertion of the tube body into the tube holder strip.

25. The reagent holding system of claim 24, wherein the ridges do not meet one another at a center of the pattern.

26. The reagent holding system of claim 24, wherein the top of the reagent tube has chamfer edges to reduce expansion of the top rim of the tube during heat sealing of a foil on the top of the tube.

27. The reagent holding system of claim 24, wherein the cooperating structure comprises a snap tab.

28. A reagent tube for insertion into a tube holder strip, comprising:
a tube body having a top, a bottom, and an interior surface, wherein the top, bottom, and interior surface of the tube body define a volume configured to hold a liquid;
a radially-extending lip configured for locking engagement with cooperating structure on a tube holder strip to retain the tube after insertion into the tube holder strip, the lip comprising a top surface proximal to the top of the tube body, a bottom surface opposite the top surface, a radial wall extending between the top and bottom surface of the lip, and a beveled edge located at the junction of the top surface and the radial wall;
a pattern of convex ridges extending radially and centered at the bottom of the interior surface of the tube, wherein the convex ridges extend vertically from the bottom interior surface of the tube body, wherein the pattern of ridges and the ridges are configured to enable pipetting of substantially all of the liquid held in the reagent tube; and
a ring centered at the bottom of the interior surface of the tube, wherein the pattern of radially extending convex ridges intersect the ring.

29. The tube of claim 27, wherein the ridges do not meet one another at a center of the pattern.

30. The reagent tube of claim 27, where the top of the reagent tube has chamfer edges to reduce expansion of the top rim of the tube during heat sealing of a foil on the top of the tube.

31. The reagent tube of claim 27, wherein the width of the radial lip is at least twice as large as the thickness of the radial lip.

* * * * *